United States Patent
Prak et al.

(10) Patent No.: US 7,582,263 B2
(45) Date of Patent: Sep. 1, 2009

(54) UNIVERSAL INTERFACE FOR A MICRO-FLUIDIC CHIP

(75) Inventors: Albert Prak, Enschede (NL); Hendrik Harmen van den Vlekkert, Haaksbergen (NL)

(73) Assignee: Octrolix BV (NL)

( * ) Notice: Subject to any disclaimer, the term of this patent is extended or adjusted under 35 U.S.C. 154(b) by 812 days.

(21) Appl. No.: 11/044,542

(22) Filed: Jan. 27, 2005

(65) Prior Publication Data
US 2006/0163069 A1 Jul. 27, 2006

(51) Int. Cl.
- *B01L 3/00* (2006.01)
- *G01N 27/327* (2006.01)
- *G01N 27/453* (2006.01)

(52) U.S. Cl. ............... 422/99; 204/403.01; 204/601
(58) Field of Classification Search .................. 204/403.01–403.15, 600, 601; 422/99, 100
See application file for complete search history.

(56) References Cited

U.S. PATENT DOCUMENTS

| 6,526,823 B2 * | 3/2003 | Tai et al. ........... 73/204.26 |
| 2002/0015667 A1 | 2/2002 | Chow | |

FOREIGN PATENT DOCUMENTS

DE 103 18 219 A1 11/2004

WO WO 00/78456 A1 * 12/2000

OTHER PUBLICATIONS

Africa S—Synthesis System, Africa Automated Flow Reaction Incubation & Control Apparatus, Jan. 27, 2005, http://www.syrris.com/Syrris_files/slide0120.htm.
LabChip Systems, Caliper LifeSciences, Jan. 27, 2005, http://www.caliperls.com/products/labchip_systems.shtml.
Africa Modular Synthesis and Optimisation System (product data sheet), Africa Automated Flow Reaction Incubation & Control Apparatus, copyright 2004, Syrris.
Capillary/Chip Electrophoresis, Capillary/Chip Electrophoresis Glass Chips, Nov. 23, 2004, http://www.micronit.com/products/glasschips/capillaryelectrophoresis.html.

* cited by examiner

*Primary Examiner*—Alex Noguerola
(74) *Attorney, Agent, or Firm*—DeMont & Breyer, LLC (57) ABSTRACT

An integrated capillary electrophoresis system comprising a universal interface is disclosed. The universal interface includes one or more of the following structural elements: a chip assembly that receives a capillary electrophoresis CE chip; a fluidic interface for coupling fluids between the chip assembly and external sources or destinations; a first electrical interface for coupling power from an external source to the chip assembly; a second electrical interface for coupling electrical signals from the chip assembly to external analysis electronics; an optical interface for coupling optical signals between the chip assembly and external sources or destinations; and a docking station for uniting and spatially locating the various other structural elements.

20 Claims, 8 Drawing Sheets

UNIVERSAL INTERFACE FOR A MICRO-FLUIDIC CHIP

FIELD OF THE INVENTION

The present invention relates to micro-fluidic chips in general, and, more particularly, to fluidic, electrical and optical interfaces for use with micro-fluidic chips.

BACKGROUND OF THE INVENTION

The term "micro-fluidics" refers to technologies that involve the manipulation of very small amounts (typically nano-liter to micro-liter quantities) of liquids or gases. Micro-fluidic technologies are now used to carryout a variety of chemical and biological processes. Many benefits are realized by conducting these types of processes at the micro-scale. In short, there are things that can be done at the micro-scale that simply cannot be done, or cannot be done as quickly, cheaply, precisely, or as safely with macro-scale process configurations.

Micro-fluidic processes are usually conducted in a network of micro-channels. These micro-channels, which are typically only tens of microns deep and wide, are usually formed via lithographic processing and chemical etching. The network of channels is typically formed in a postage stamp-sized glass, polymer, or silicon substrate.

In addition to the network of micro-channels, some micro-fluidic systems include mixers, reservoirs, diffusion chambers, heaters, integrated electrodes, pumps, valves, and the like. The phrase "lab-on-a-chip" has been coined to refer to these integrated micro-fluidic systems, which are capable of conducting chemical reactions, high-throughput screening and drug discovery, DNA amplification in genomics, and cell screening, counting, and sorting and biochemical monitoring.

One important application for lab-on-a-chip is "capillary electrophoresis." Using capillary electrophoresis, substances are separated on the basis of variations in the velocities of charged particles (i.e., electrophoretic mobility) in a conducting fluid as they migrate under the influence of an electric field. Capillary electrophoresis has successfully been employed in the analysis of DNA fragments and other biomolecules. Using certain modifiers, it is even possible to separate neutral solutes.

Figure 1A:
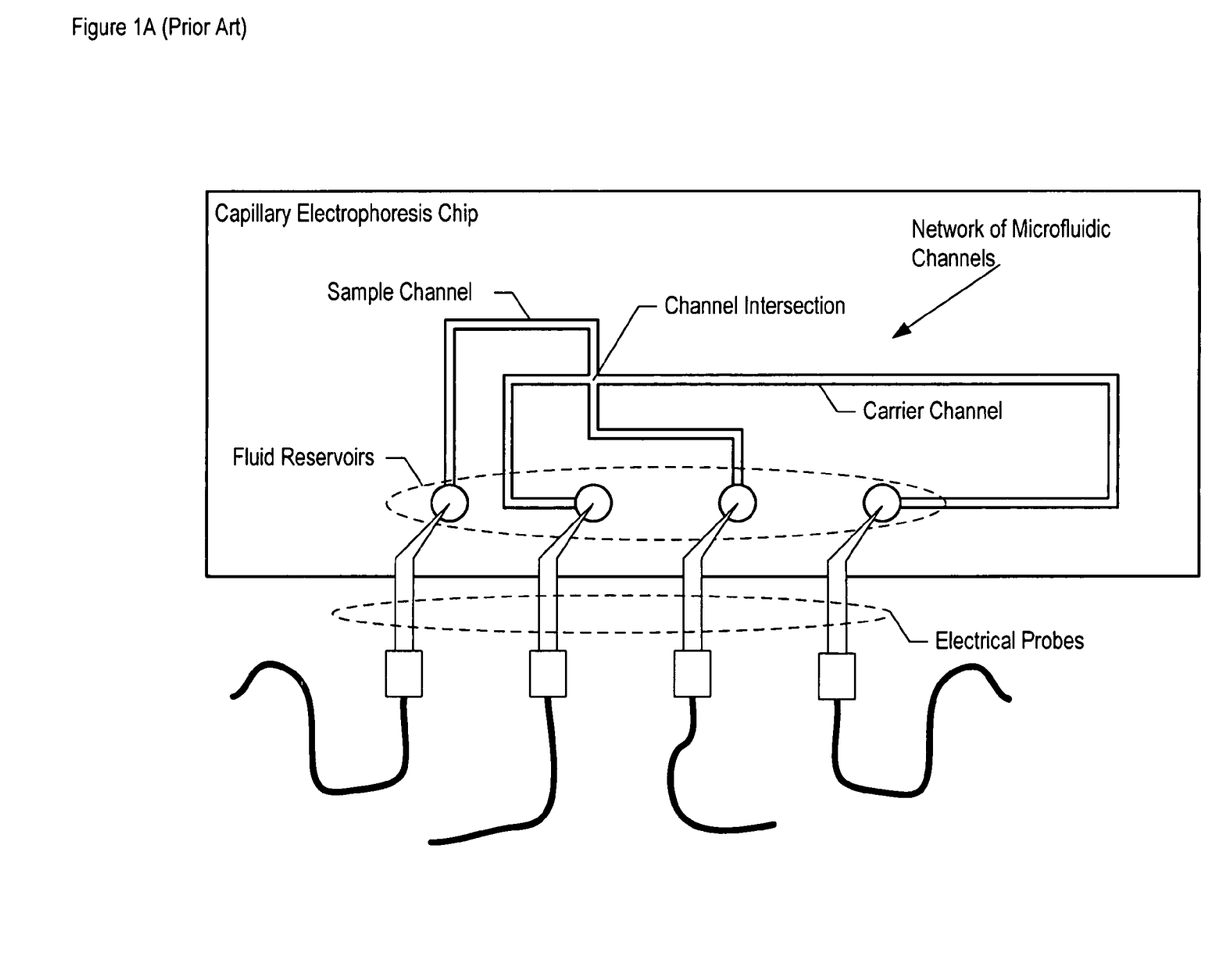
FIG. 1A depicts a prior-art capillary electrophoresis chip.

FIG. 1A depicts an example of a typical capillary electrophoresis ("CE") chip. The CE chip includes a network of micro-fluidic channels. In the example that is depicted in FIG. 1A, the network comprises a sample channel and a carrier channel. A sample of fluid to be tested is introduced into the network at one of the sample-channel reservoirs. The sample is usually added to the reservoirs via a syringe. The sample flows through the sample-channel via capillary action. A carrier, such as saline, glucose, etc., and usually a pH buffer are introduced into the network at one of the carrier-channel reservoirs.

A high voltage, usually in excess of few hundred volts and sometimes above thousand volts, is applied for a brief period (i.e., in the range of a few seconds to a few minutes) between the reservoirs via electrical probes. This induces an electro-osmotic flow, which is used to launch a small plug of the sample fluid into the carrier channel at the intersection of the two channels. The various charged species in the small sample will stratify in the carrier channel as a consequence of differences in electrophoretic mobility. At a certain location, the fluid in the carrier channel is interrogated (e.g., optically, electrically, etc.). Due to stratification, the various species will pass the detection location at different times. This provides a means for resolving the various species within the sample.

While the CE chip provides an efficient platform for conducting capillary electrophoresis, there are drawbacks associated with its use. In particular, little attention has been paid to fluid and power management; these resources are not efficiently integrated with the CE chip. Since sample and carrier fluids are manually added to the CE chip via syringes, the chip cannot be sealed. This presents a risk of contamination. Furthermore, the application of high voltage via external electrodes presents a safety hazard. Additionally, the prevailing ad-hoc approach to supplying fluid and power to the CE chip also raises concerns about the reproducibility of results. And, more generally, the current approach to capillary electrophoresis is so cumbersome and inconvenient that, notwithstanding its utility for any particular analysis application, there is a reluctance to use the technique.

SUMMARY OF THE INVENTION

The present invention enables the use of micro-fluidic technologies, including those that incorporate lab-on-a-chip devices, without some of the costs and disadvantages of the prior art.

For example, in the illustrative embodiment, the invention is applied to a capillary electrophoresis process to provide an integrated capillary electrophoresis system ("integrated CE system"). The integrated CE system comprises a universal interface that addresses one or more of the following issues related to the use of CE chips:
 fluid management;
 power management;
 electrical interference;
 safety;
 physical contamination; and
 convenience.

In the illustrative embodiment, the universal interface comprises one or more of the following structural elements:
 a chip assembly that receives the CE chip and provides electromagnetic shielding for any electrical components within;
 a fluidic interface for coupling fluids between the chip assembly and external sources or destinations;
 a first electrical interface for coupling electrical energy from an external source to the chip assembly;
 a second electrical interface for coupling electrical signals from the chip assembly to external analysis electronics;
 an optical interface for coupling optical signals between the chip assembly and external sources or destinations; and
 a docking station for uniting and spatially locating the various other structural elements of the integrated CE system.

In accordance with the illustrative embodiment, the chip assembly includes ports, conductors, ferrules, etc., which, in conjunction with other elements of the universal interface, couple the CE chip to external sources (e.g., of fluid, of power, of optical signals, etc.) and external destinations (e.g., analysis electronics, etc.). In some embodiments, the chip assembly includes electronics that support or are otherwise associated with sensors that are disposed on the CE chip (e.g., electrical conductivity sensor, etc.).

In accordance with the illustrative embodiment, the docking station receives the chip assembly as well as the fluidic interface, the electrical interfaces, and if present, the optical interface. As indicated above, the fluidic interface couples fluids (e.g., liquid, gas, etc.) between the chip assembly and external sources or external destinations. The optical interface couples optical signals between the chip assembly and external sources or external destinations. The first electrical interface couples electrical energy to the chip assembly and the second electrical interface couples electrical signals from the chip assembly to external destinations.

The integrated CE system, by virtue of the universal interface in accordance with the illustrative embodiment of the present invention, provides a simplicity and convenience that has been unavailable in the prior art. In particular, the fully-integrated CE system is a "plug-and-play-" type assemblage that is formed by simply pressing together the various structural elements. In this regard, the docking station serves as a "locating" element that receives the other elements and fixes them in correct spatial orientations to create fluidic, electrical, and optical paths between the CE chip and external sources or destinations. The external sources/destinations are then coupled to easily accessed ports or connections of the assemblage. This is in contrast to some prior-art systems in which fluid is introduced to the CE chip via syringes and power delivery and signal read-out is performed via hand-held probes.

Furthermore, since most prior-art systems are open and syringe-operated, they are most suitable for lab environments and require human or robotic intervention. On the other hand, an integrated CE system in accordance with the illustrative embodiment is suitable for in-line applications. For example, the system can be used in unattended field applications.

In some embodiments, the chip assembly and fluidic interface of the universal interface are self sealing, so that when external sources are disconnected from the fluidic interface, or when the chip assembly is not engaged to the docking system, the CE chip remains isolated from the external environment.

In some embodiments, the integrated CE system incorporates EMI shielding. The shielding improves the performance of the CE chip in embodiments in which an EC sensor, or other type of electromagnetic sensor, is incorporated in the CE chip.

In the illustrative embodiment, the universal interface is used in conjunction with a CE chip to provide the integrated CE system. In other embodiments, however, the universal interface is used in conjunction with other micro-fluidic processes or other types of lab-on-a-chip devices. Those skilled in the art, after reading the present disclosure, will know how to adapt or otherwise modify, to the extent necessary, universal interface disclosed herein for use with other types of micro-fluidic processes and other lab-on-a-chip devices.

DETAILED DESCRIPTION

The illustrative embodiment of the present invention is an integrated capillary electrophoresis system comprising a universal interface and a CE chip. The CE chip is a lab-on-a-chip type device on which the capillary electrophoresis process is conducted. The universal interface enables the operation of the system by facilitating the transfer of one or more of: fluids, electrical energy, and electrical and optical signals between the external environment and the CE chip.

This disclosure begins with a description of the CE chip 100. In accordance with the illustrative embodiment, the CE chip is coupled to the universal interface to provide an integrated CE system. The elements of the universal interface are depicted in FIGS. 3, 4A-4D, 5, 6, and 7A-7D. But before these elements are described, context is provided by way of the block diagram of FIG. 2, which depicts the integrated CE system coupled to a variety of auxiliary systems for conducting a capillary electrophoresis process.

Figure 1B:
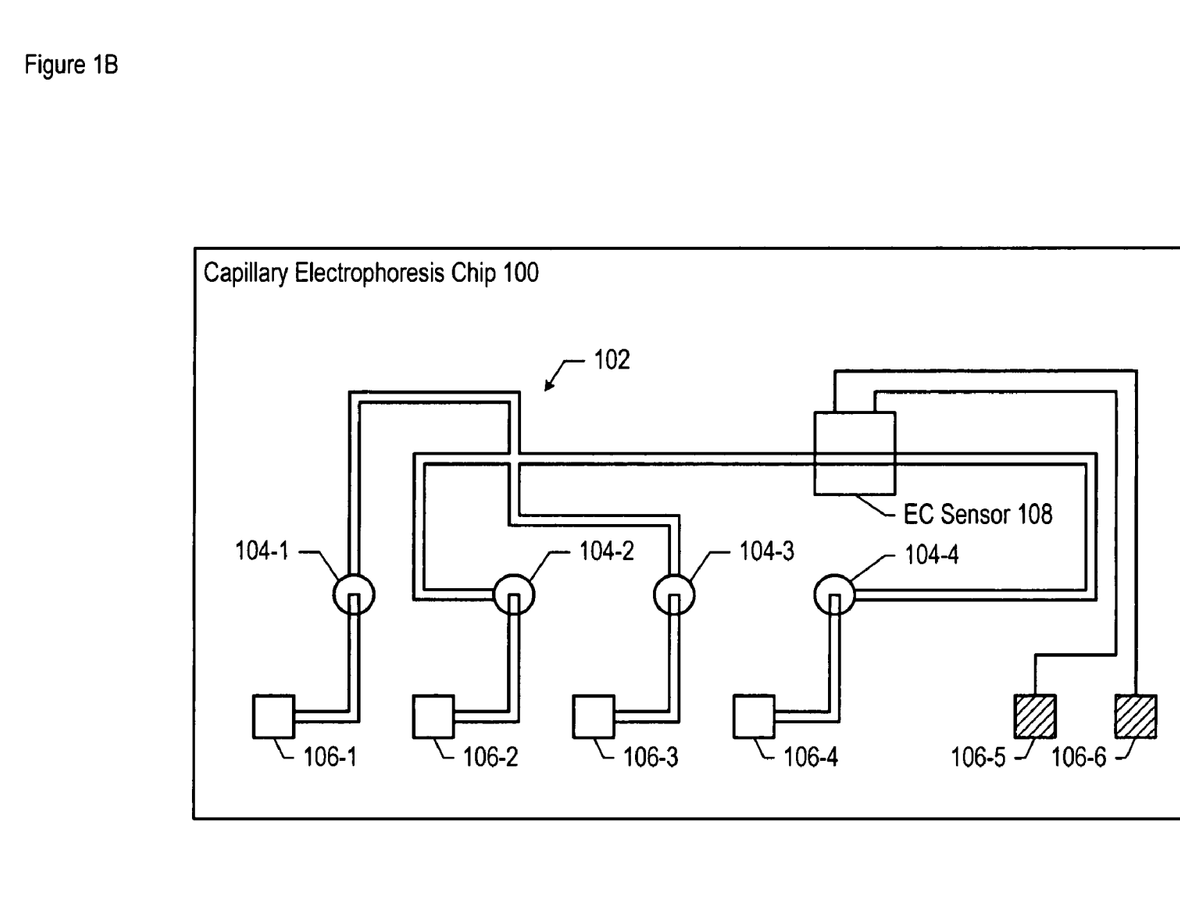
FIG. 1B depicts a capillary electrophoresis chip for use in conjunction with the illustrative embodiment of the present invention.

Beginning now the description of CE chip 100, and with reference to FIG. 1B, CE Chip 100 includes network 102 of subsurface micro-fluidic channels within a block of glass, polymer, etc. The network includes a sample channel, which is defined between reservoirs 104-1 and 104-3, and a carrier channel, which is defined between reservoirs 104-2 and 104-4. Fluid is introduced into the reservoirs via ports (not depicted) that extend through the material that overlies network 102. Electrical contact pads 106-1 through 106-4 are electrically coupled to respective reservoirs 104-1 through 104-4. The electrical contact pads serve as an interface on CE chip 100 for applying high voltage (i.e., a few hundred to a thousand or more volts) for a brief period of time (i.e., a few seconds to a few minutes) to the fluid in the reservoirs.

CE chip 100 also includes electrical conductivity ("EC") sensor 108. The EC sensor interrogates the fluid flowing through the carrier channel. As described in the Background section of this specification, a small amount of sample fluid from the sample channel is introduced into the carrier channel. The various charged species contained in this sample stratify in the carrier channel under the influence of an electric field as a consequence of differences in their electrophoretic mobility. The fluid in the channel will therefore have a time-varying electrical conductivity, which is sensed by EC sensor 108. Electrical contact pads 106-5 and 106-6 serve as sense electrodes for a sensing signal that is generated by EC sensor 108.

In some other embodiments, other types of sensors are integrated into CE chip 100. These other types of sensors sense other properties of the fluid, such as optical properties, magnetic properties, transport properties, and so forth. After reading this disclosure, those skilled in the art will be able to suitably adapt the integrated CE system described herein, to the extent required, to use with a CE chip having other types of sensors.

In yet some additional embodiments, an externally-sourced signal (typically, but not necessarily, an optical signal) is directed toward CE chip 100 to interrogate the fluid. This involves passing the signal through the fluid, which alters the signal. The altered signal is then directed to an external sensor/detector.

Figure 2:
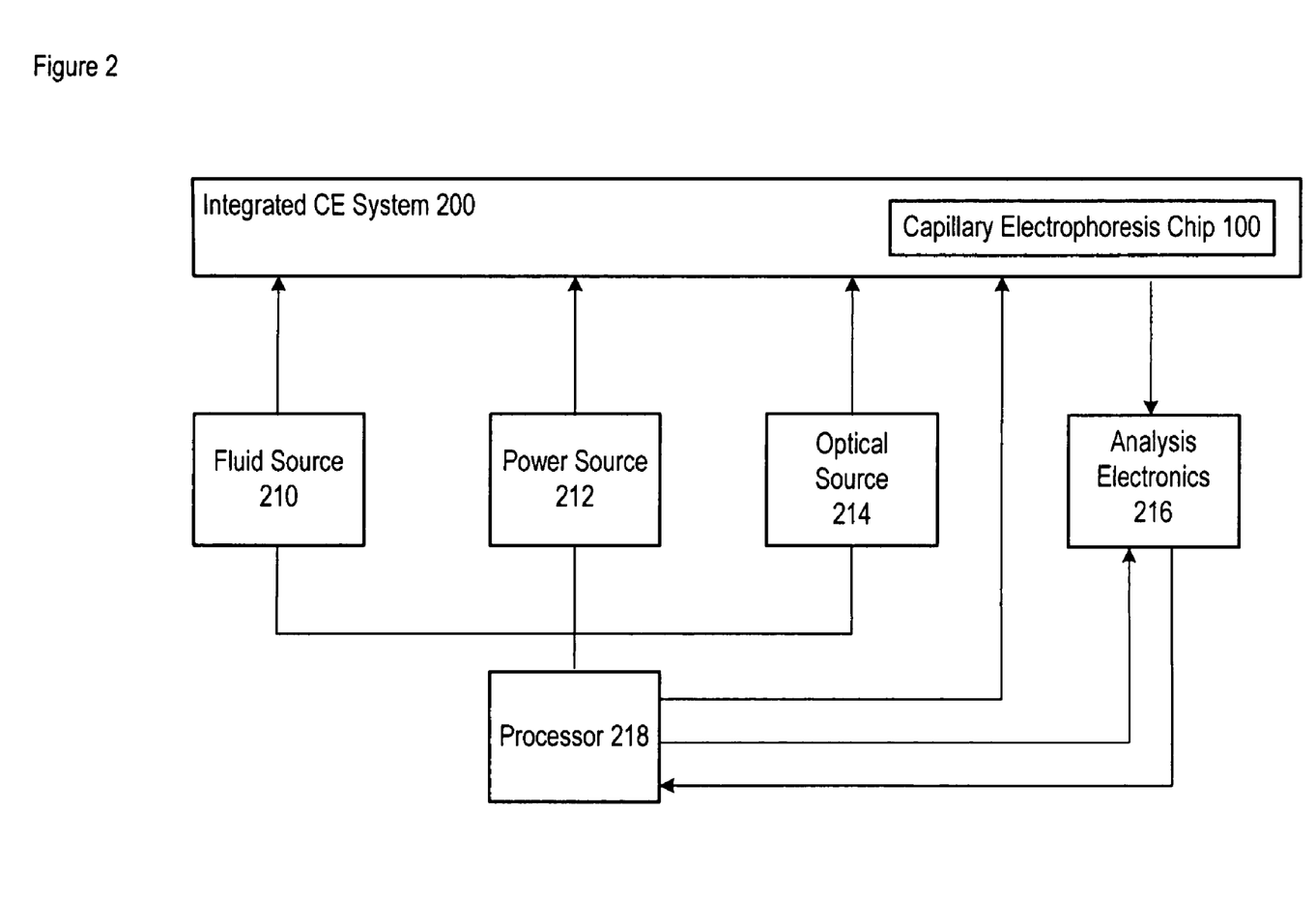
FIG. 2 depicts a system for carrying out a capillary electrophoresis process, including integrated capillary electrophoresis system 200 comprising a universal interface in accordance with the illustrative embodiment of the present invention.

As previously mentioned, CE chip 100 is coupled to one or more elements of the universal interface to form integrated CE system 200. The integrated system must then be coupled to sources of fluid, power, etc., as required to conduct the capillary electrophoresis process. FIG. 2 depicts the integrated CE system coupled to these external sources as well as other auxiliary systems for conducting a capillary electrophoresis process.

As depicted in FIG. 2, integrated CE system 200 receives fluid from external fluid source 210, high-voltage electricity from external power system 212, and, in some embodiments, optical signals from external optical source 214. The optical signal can be used, for example, to optically interrogate the fluid in the carrier channel of CE chip 100 within integrated CE system 200.

Analysis electronics 216 (e.g., detector, etc.) receives a signal from CE chip 100. The signal, which can be optical, electrical, etc., provides information concerning the various species in the fluid. Analysis electronics 216 suitably processes the signal to obtain an analysis of the fluid.

As desired, processor 218 is used to control any one or more of: fluid source 210, power source 212, optical source 216, any devices within CE system 200 (e.g., EC sensor 108, etc.), and analysis electronics 218.

Having provided context for integrated CE system 200, the various elements of the universal interface will now be described.

Figure 3:
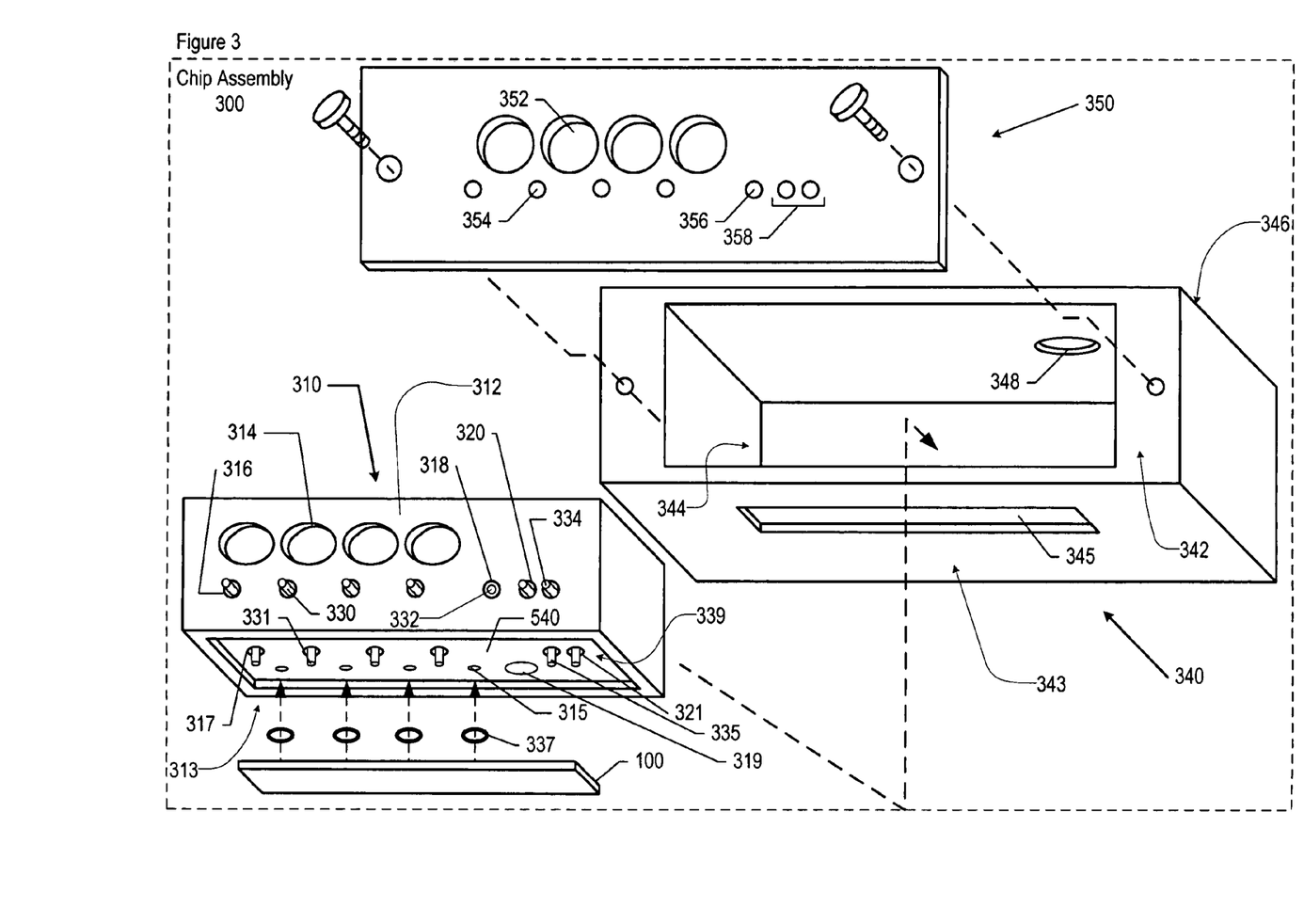
FIG. 3 depicts a chip assembly, which is one of the elements of system 200 and of the universal interface.

FIG. 3 depicts, via an exploded, perspective view, chip assembly 300 of integrated CE system 200. Chip assembly 300 comprises chip interface 310, chip-interface housing 340, and housing face plate 350.

Chip interface 310 couples fluid, electrical energy, and electrical and optical signals between CE chip 100 and other elements of the universal interface. In the illustrative embodiment, chip interface 310 is a solid block of material in which various ports and other features are formed. The material from which chip interface 310 is formed will advantageously possess at least some of the following properties: high strength & toughness, low flammability, desirable electrical properties, easily processed, chemically resistant, and impact and wear resistant. In some embodiments, this material is a high-performance thermoplastic, such as poly(etheretherketone) ("PEEK"), with or without the usual fiber reinforcements (e.g., glass, carbon, or Kevlar).

For clarity of explanation, chip interface 310 is characterized as having first face 312 and second face 313. The second face includes recess or cavity 339. This recess receives CE Chip 100. Inputs required for CE chip 100, such as fluid, electrical energy, and the like, are received at first face 312 of chip interface 310. Inputs that are received at the first face are "automatically" coupled toward second face 313 and CE chip 100.

At the CE chip, fluid is delivered to the reservoirs (see, e.g., reservoir 104-1, etc., at FIG. 1B) and high-voltage electricity is delivered to the electrical contact pads (e.g., 106-1, etc.). The optical signal, if present, can be directed toward the carrier channel for interrogation. It will be understood that, as required, fluid or electrical or optical signals can be withdrawn from CE chip 100 for delivery to external destinations. In such cases, they will flow from CE chip 100, to face 313, and then to face 312. In other words, fluid, electrical energy, etc. can flow in either direction through chip interface 310.

Chip interface 310 is now described in further detail to clarify how fluid, electrical energy, etc. is coupled between the first face and the second face and, ultimately, to CE chip 100.

Figure 4A:
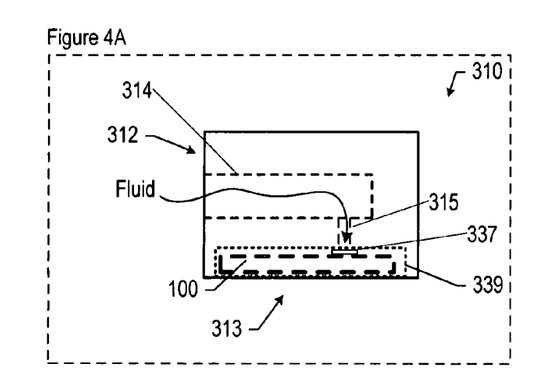
FIG. 4A depicts further detail of the fluidic management system on the chip assembly.

With reference now to FIGS. 3 and 4A, first face 312 includes four ports 314 and second face 313 has four ports 315. As depicted in FIG. 4A, these ports, which are hereinafter referred to as "fluidic ports," are physically coupled to one another. As a consequence, they create a fluidic link between first face 312 and second face 313 of chip interface 310.

FIG. 4A also depicts CE chip 100 positioned within recess 339 of the chip interface. O-ring 337 is disposed between CE chip 100 and port 315 to prevent leakage of fluid (see also, O-rings 337 in FIG. 3). In some embodiments, CE chip 100 includes an integrated gasket, such as a screen-printed gasket, rather than a separate o-ring.

Figure 4B:
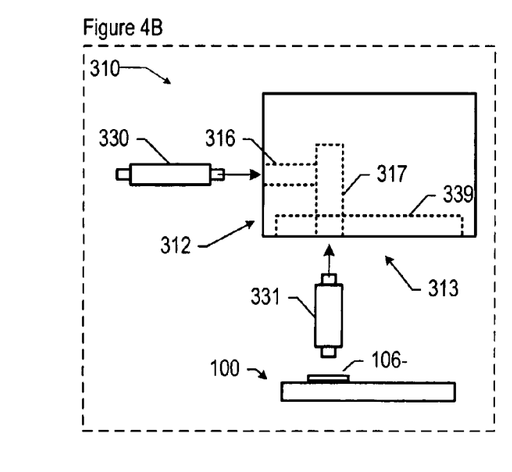
FIG. 4B depicts further detail of the electrical management system on the chip assembly.

Referring now to FIGS. 3 and 4B, first face 312 of chip interface 310 also includes four ports 316, which contain conductors 330. Second face 313 includes four ports 317, which contain conductors 331. As depicted in FIG. 4B, these ports are physically coupled to one another. Conductors 330 and 331 within these ports are in physical contact, thereby creating an electrical link between first face 312 to second face 313. (In FIG. 4B, conductors 330 and 331 are depicted outside of the ports and CE chip is depicted outside of recess 339 for clarity.) In the illustrative embodiment, conductors 330 and 331 carry high voltage electricity through chip interface 310 to CE chip 100. Conductors 330 and 331 are hereinafter referred to as "high-voltage electrical conductors."

In the illustrative embodiment depicted in FIG. 4B, conductors 330 and 331 are implemented as spring contacts. The spring contact within port 317 contacts an electrical contact pad (see, e.g., electrical contact pad 106-1 in FIG. 1B) on CE chip 100. This creates an electrical pathway from first face 312 to CE chip 100.

Figure 4C:
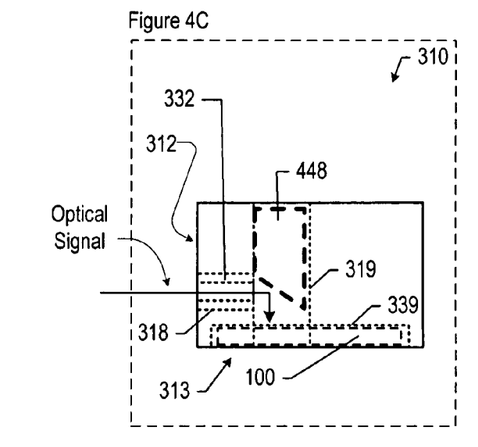
FIG. 4C depicts further detail of the optical management system on the chip assembly.

Referring now to FIGS. 3 and 4C, first face 312 of chip interface 310 further includes port 318, which contains ferrule sleeve 332. As depicted in FIG. 4C, port 318 is physically coupled to port 319, in which mirror 448 resides. An optical signal injected into chip interface 310 at face 312 is received by mirror 448 and reflected toward face 313 and CE chip 100. Ports 318 and 319 are hereinafter referred to as "optical ports." Those skilled in the art, after reading the present disclosure, will know how to use other wave-guiding arrangements to direct an optical signal from face 312 to face 313.

With continuing reference to FIG. 3, first face 312 also includes two ports 320, which contain conductors 334. These conductors are electrically coupled to conductors 335, which protrude from two ports 321 at second face 313. In the illustrative embodiment, conductors 334 and 335 carry electrical signals from CE chip 100 through chip interface 310. For example, in the illustrative embodiment, these conductors carry electrical signals generated by EC sensor 108. Conductors 334 and 335 are hereinafter referred to as "sense-signal conductors." In the illustrative embodiment, the implementation of the sense-signal conductors and associated ports is identical to the implementation of the high-voltage electrical conductors.

As indicated in FIG. 3, chip interface 310 resides within cavity 344 of chip-interface housing 340. In some embodiments, the housing is formed from aluminum or another material that serves as an EMI-shield for any electrical devices that are disposed within chip interface 310, including any devices contained on CE chip 100.

With regard to the spatial orientation of chip interface 310 within cavity 344, first face 312 of chip interface 310 is proximal to face 342 of housing 340. The housing is sized and arranged so that when chip interface 310 is inserted within housing 340, CE chip 100 aligns with opening or optical window 345 on face 343 of housing 340. Opening 345 enables an optical signal to pass directly from CE chip 100 to a device that is external to housing 340. For example, consider an optical signal that has been delivered to CE chip 100 from optical port 319 to interrogate fluid within the carrier channel. Once the signal passes through CE chip 100, opening 345 enables the signal to exit housing 340 for processing and analyses in an external device (see, e.g., analysis electronics 216 at FIG. 2). In some embodiments in which chip-interface housing 340 is intended to serve as an EMI-shield, optical window 345 advantageously comprises a conductive material, such as indium tin oxide.

Optional hole 348 in housing 340 provides a second optical path to CE chip 100. For example, in some embodiments, an optical signal from an external source is directed through hole 348 in the housing and into optical port 319 (rather inserting an optical fiber into chip interface 310 at first face 312).

Face plate 350 is attached to chip-interface housing 340 at face 342 thereby fully enclosing chip interface 310. Face plate 350 includes appropriately-sized and located holes 352, 354, 356, and 358 that align with the various ports and conductors on chip interface 310. As a consequence, fluidic, electrical, and optical communication can be established between chip interface 310 and other elements of the universal interface that are external to housing 340. To facilitate such communication, high-voltage electrical conductors 330, sense-signal conductors 334, and ferrule sleeve 332 extend slightly beyond face plate 350 when it is attached to housing 340.

The integration of chip assembly 300 with other elements of integrated CE system 200 is described with reference to FIGS. 5, 6, and 7A-7B.

Figure 5:
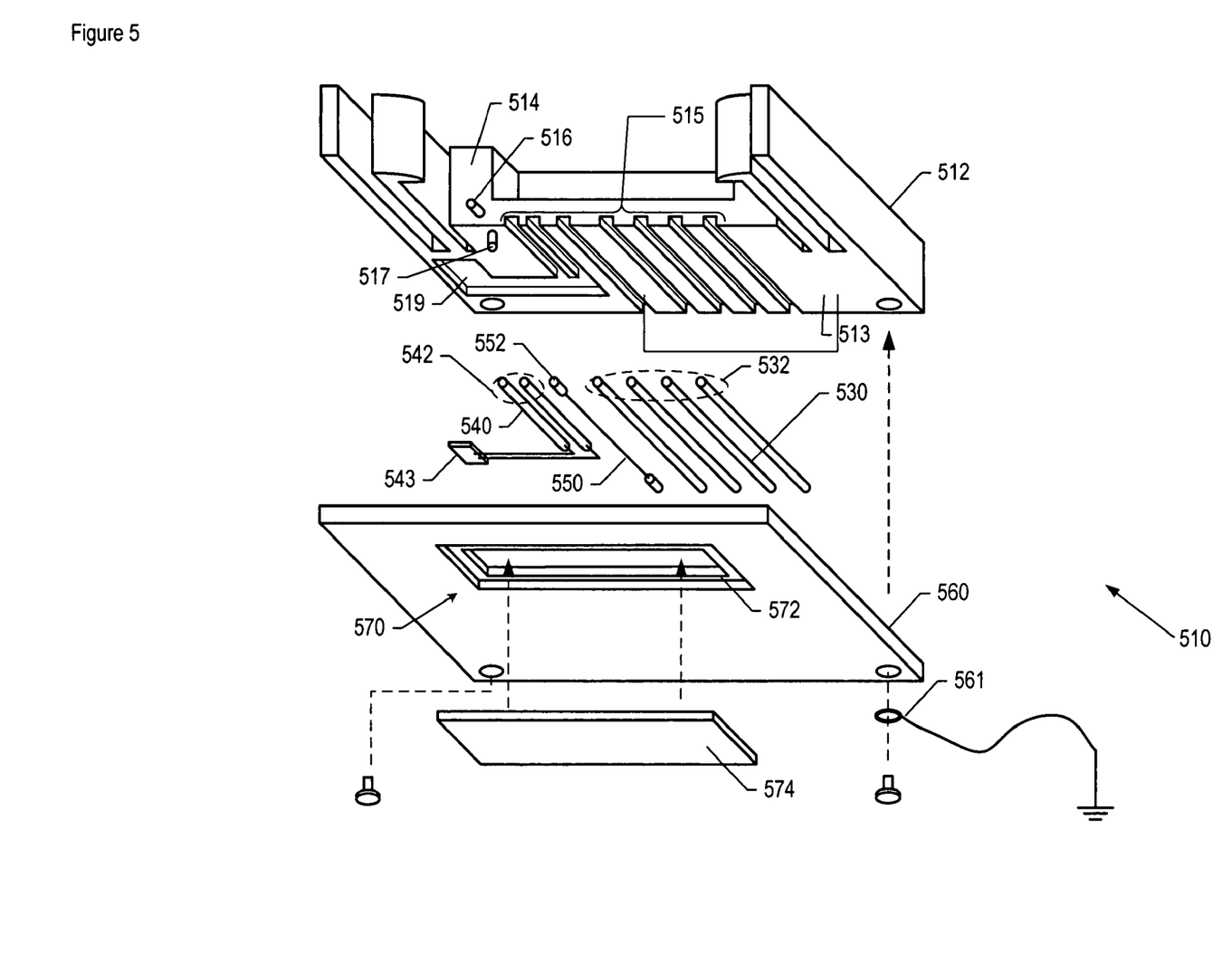
FIG. 5 depicts a docking station, electrical interfaces, and optical interface, which are elements of system 200 and of the universal interface.
Figure 6:
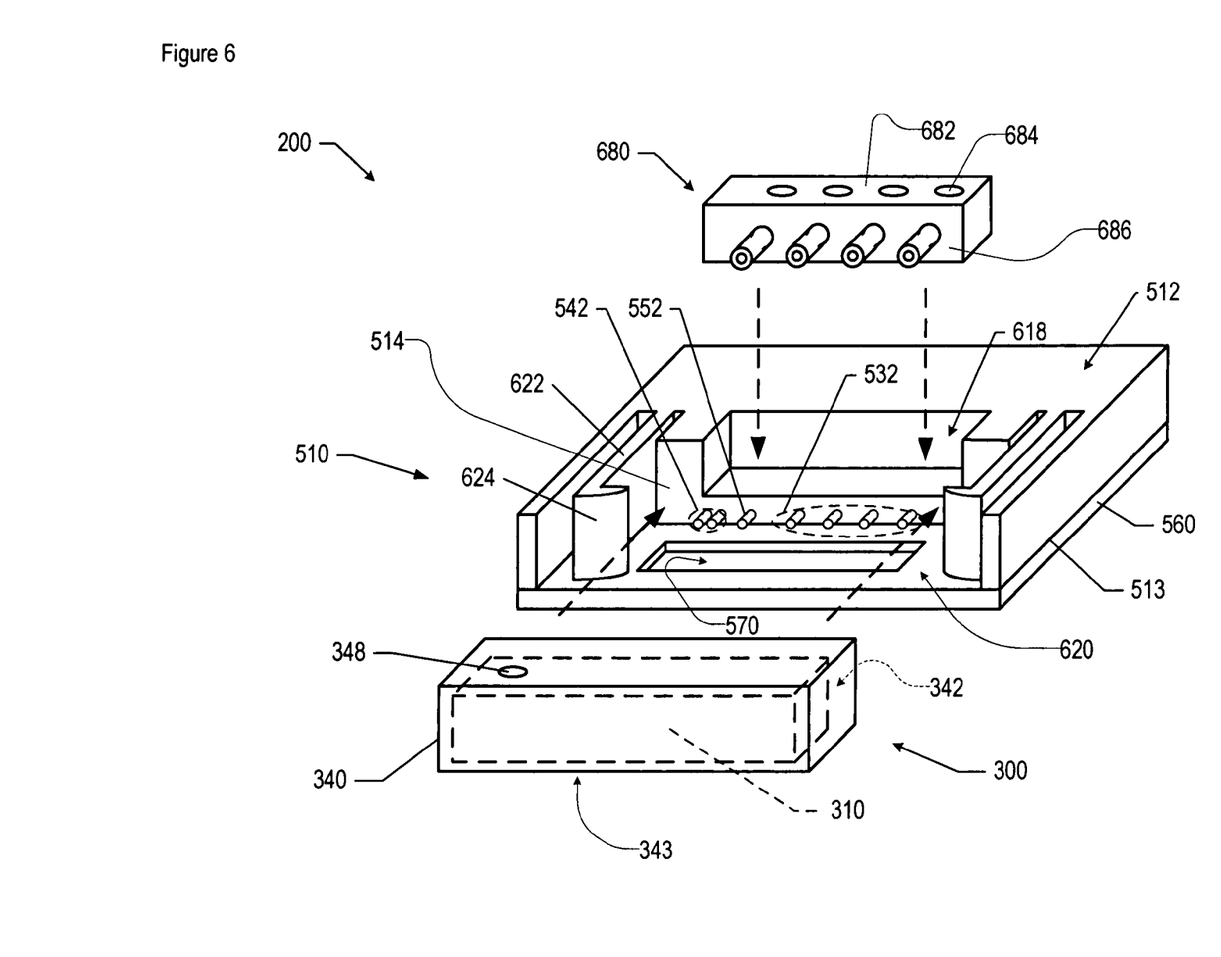
FIG. 6 depicts the manner in which the elements of the universal interface cooperate with CE chip 100 to form system 200.
Figure 7A:
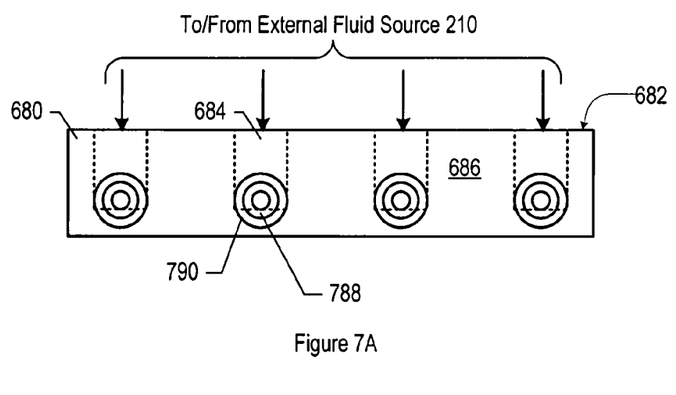
FIGS. 7A and 7B depict further detail of the fluidic interface of FIG. 5.
Figure 7B:
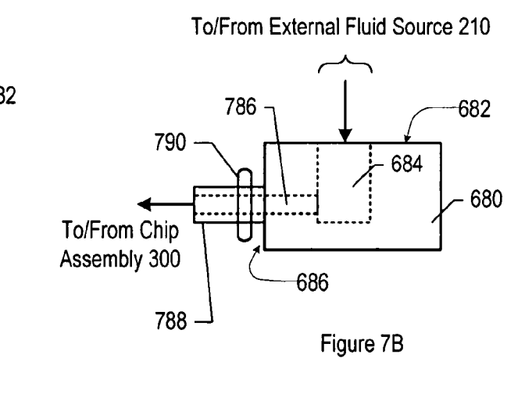

Briefly, FIG. 5 depicts a view of lower surface 513 of docking station 510, which is another element of the universal interface and integrated CE system 200. This Figure, which is an exploded, perspective view, depicts how the various electrical and optical interfaces are coupled to docking station 510. FIG. 6 depicts the coupling of fluidic interface 680 to docking station 510 and the manner in docking station secures and locates chip assembly 300 with respect to the various interfaces to create the desired fluidic, electrical and optical pathways to CE chip 100 within the chip assembly. FIGS. 7A-7B depict further external and internal details of fluidic interface 680.

Referring now to FIGS. 5 and 6, docking station 510 has upper surface 512 and lower surface 513. The lower surface of docking station 510 includes a plurality of channels 515. These channels receive conductors 530, conductors 540, and optical fiber 550. As depicted in FIG. 6, conductors 530 terminate beyond wall 514. The terminal portion of conductor 530 is high-voltage electrical interface 532 between external power source 212 and chip assembly 300. Similarly, conductors 540 terminate beyond wall 514 at electrical-signal interface 542, which is the electrical-signal interface between analysis electronics 216 and chip assembly 300. Ferrule 552 is coupled to the end of optical fiber 550 that terminates beyond wall 514. Ferrule 552 serves as the optical interface between optical source 214 and chip assembly 300.

Channels 515 that receive conductors 540 lead to cavity 519. Cavity 519 receives amplifier 543 that is electrically coupled to conductors 540. The amplifier amplifies the signal that is generated by EC sensor 108 on CE chip 100. The amplified signal is then transmitted to externally-located analysis electronics 216 (see FIG. 2).

Conductors 530 and 540 and optical fiber 550 are secured within channels 515 via cover plate 560. The cover plate is attached to lower surface 513 of docking station 510 via screws. Cover plate 560 includes optical window 570, which comprises opening 572 and optically-transparent (at least at wavelengths of interest) plate 574. Opening 572 is suitably machined (e.g., with a lip, etc.) for receiving plate 574. In some embodiments, plate 574 comprises glass.

In some embodiments, docking station 510 is formed from the same material as is used for chip interface 310, e.g., PEEK, etc. Since cover plate 560 is intended, in at least some embodiments, as an EMI shield, plate 574 should be conductive, such as by applying a coating of indium tin oxide.

As depicted in FIG. 6, chip assembly 300 and fluidic interface 680 couple to upper side 512 of docking station 510. More particularly, fluidic interface 680 is received within region 618 of docking station 510. The fluidic interface is sized for relatively tight-fitting engagement within region 618 such that the left and right sidewalls, back wall, and bottom surface of fluidic interface 680 abut the walls that define region 618. Like docking station 510, fluidic interface 680 can be formed from the same material as is used for chip interface 310, e.g., PEEK, etc.

Fluid from external source(s) is received by four fluidic ports 684 at upper surface 682 (hereinafter "inlet face 682") of fluidic interface 680. Fluid received at the inlet face is "automatically" routed to front side 686 (hereinafter "outlet face 686") of the fluidic interface. While fluidic interface 680 is typically used to deliver fluid to chip assembly 300, it can also receive fluid from the chip assembly. In the illustrative embodiment, the inlet face and the outlet face of fluidic interface 680 are orthogonal to one another.

FIGS. 7A and 7B depict respective front and side views of fluidic interface 680, showing additional external and internal details. As depicted in FIG. 7B, each port 684 is physically coupled to port 786 thereby creating a fluidic path between inlet face 682 to outlet face 686. Each port 786 terminates at nozzle 788. O-ring or gasket 790 is disposed on each nozzle 788 (to form a seal when inserted into fluidic ports 314 on chip interface 310).

Docking station 510 receives chip assembly 300 at region 620, which is the region defined by wall 514, flexible restraining arms 622, restraints 624, and bottom cover 560.

To couple chip assembly 300 to docking station 510, the chip assembly is pushed into restraints 624. Restraining arms 622 flex under the applied force, thereby admitting chip assembly 300 into region 620. Once the chip assembly clears restraints 624, restraining arms 622 snap back in place, thereby securing the chip assembly to docking station 510. Restraining arms 622 and restraints 624 therefore function as a passive restraint system.

In the illustrative embodiment, both docking station 510 and chip assembly 300 include electrical devices (i.e., preamp 544 and EC sensor 108). As a consequence, it is desirable to shield and ground both the docking station and the chip assembly. To this end, docking station 510 includes ground pins 516 and 517. Ground pin 517 contacts conductive cover plate 560. The cover plate is coupled to ground via ground wire 561. When chip assembly 300 is coupled to docking station 510, one of the screws that attaches face plate 350 to chip-interface housing 340 contacts ground pin 516. This arrangement grounds both chip assembly 300 and docking station 510.

When engaged to docking station 510 as described above, face plate 350 of chip assembly 300 opposes the various fluidic, electrical, and optical interfaces that are coupled to the docking station. As a consequence:

- Fluidic ports 314 at first face 312 of chip interface 310 fluidically couple to nozzles 788 on outlet face 686 of fluidic interface 680.
- High-voltage electrical conductors 330 at first face 312 of chip interface 310 electrically couple to high-voltage electrical interface 532 at wall 514.
- Sense-signal conductors 334 at first face 312 of chip interface 310 electrically couple to electrical-signal interface 542 at wall 514.
- Ferrule sleeve 332 at first face 312 of chip interface 310 optically couples to optical interface 552 at wall 514.

With fluidic, electrical and optical interfaces coupled to docking station 510, fluidic, electrical, and optical paths to CE chip 100 are established by simply inserting chip assembly 300 into the docking station. The establishment of the electrical paths is facilitated by the use of spring contacts, as depicted in FIG. 4B.

In the illustrative embodiment, by virtue of the spatial orientation of the various elements of the universal interface, all inputs to CE chip 100 are received at a single face—face 342—of chip assembly 300 (and at a single face—first face 312—of chip interface 310).

When chip assembly 300 is coupled to docking station 510, optical window 345 in chip-interface housing 340 aligns with optical window 570 in the docking station. This arrangement enables CE chip 100 to be directly optically interrogated by external devices.

Figure 7C:
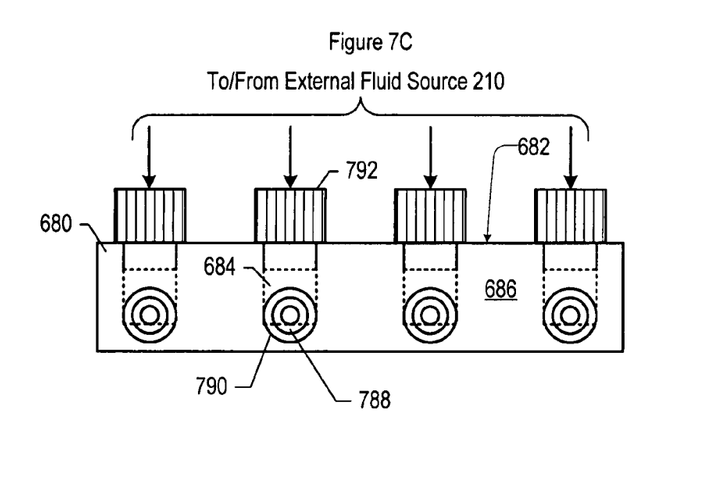
FIGS. 7C and 7D depict a further embodiment of the fluidic interface of FIGS. 7A and 7B, wherein the fluidic interface includes a self-sealing connector.
Figure 7D:
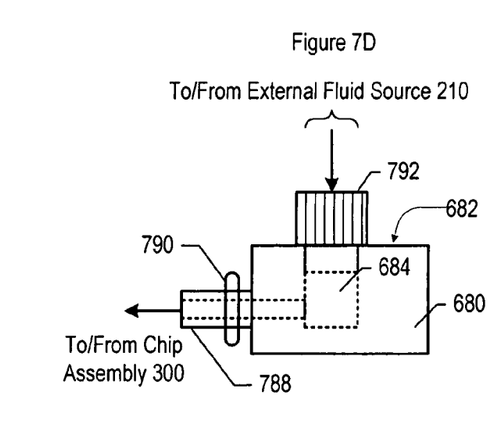

To maintain environmentally integrity when fluidic interface 680 is decoupled from external fluid source 210, fluidic interface 680 is provided with self-sealing fluidic connectors. FIGS. 7C and 7D depict fluidic interface 680 fitted with self-sealing fluidic connectors 792. Any of a variety of self-sealing connectors, which are well known in the art, can be used for this purpose.

Figure 4D:
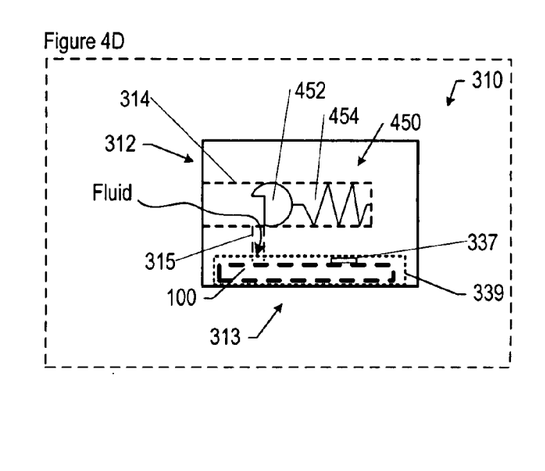
FIG. 4D depicts the fluidic management system of FIG. 4A with a self-sealing port.

Likewise, to maintain environmental integrity when chip assembly 300 is not coupled to docking station 510, in some embodiments, fluidic ports of chip interface 310 are self sealing. FIG. 4D provides a figurative representation of a self-sealing port, wherein spring-loaded sealing mechanism 450 is disposed in fluidic port 314 of chip interface 310. When nozzle 788 of fluidic interface 680 couples to fluidic port 314, plug 452 is pushed back, uncovering the entrance to fluidic port 315. This places CE chip 100 in fluid communication with an external fluid source. In this state, spring 454 is compressed. When chip assembly 300 is removed from docking station 510, the spring expands, returning plug 452 to a position in which it blocks the entrance to fluidic port 315, sealing off CE chip 100.

In the illustrative embodiment, all inputs to CE chip 100 ( i.e., fluid, electrical energy, and electrical and optical signals) are received at face 342 of chip assembly 300 (and at face 312 of chip interface 310). But in some alternative embodiments (not depicted), fluid is not received at this location. In some of those alternative embodiments, fluid is received at a surface that is orthogonal to face 342, such as at the upper surface of chip assembly 300 and chip interface 310. In other words, fluid is received at the face that is opposite to face 313 on chip interface 310. In fact, open wells are accessible via the upper surface of chip assembly 300 and chip interface 310. Syringes are typically used to deliver fluid to the open wells. In such embodiments, fluidic interface 680 (see, e.g., FIG. 6) is not required.

As previously described, in the illustrative embodiment, high-voltage is applied to contact pads 106-1 to 106-4 on CE chip 100 via high-voltage electrical conductors 330 and 331 in chip interface 310. But in some alternative embodiments, CE chip 100 does not include contact pads for applying a high voltage to the fluids within CE chip 100. In some of those alternative embodiments, high voltage is applied directly to reservoirs 104-1 to 104-4 by wires (e.g., platinum wires, etc.) that are disposed in ports 315 of chip interface 310. The wires are clamped to gold contacts, which are, in turn, electrically coupled to high-voltage electrical interface 532.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed is:

1. An apparatus comprising a universal interface, wherein the universal interface comprises:
   a chip interface, wherein the chip interface receives a microfluidic chip, and wherein the chip interface has a first face at which it receives at least one of fluid and electrical energy;
   a docking station, wherein the docking station receives the chip interface, and wherein the docking station facilitates:
      the coupling of an external source of fluid to the first face of the chip interface; and
      the coupling of an external source of electrical energy to the first face of the chip interface; and
   a fluidic interface, wherein the fluidic interface is received by the docking station, and wherein the fluidic interface comprises:
      an inlet face at which the fluidic interface receives fluid from the external source of fluid; and
      an outlet face at which the fluidic interface delivers the fluid to the first face of the chip interface, wherein the inlet face and the outlet face of the fluidic interface are orthogonal to each other.

2. The apparatus of claim 1 wherein said universal interface further comprises a first electrical interface, wherein said docking station receives said first electrical interface, and wherein said first electrical interface couples said external source of electrical energy to said first face of said chip interface.

3. The apparatus of claim 1 wherein said universal interface further comprises a second electrical interface, wherein said docking station receives said second electrical interface, and wherein said second electrical interface conducts an electrical signal from said first face of chip interface to an external destination.

4. The apparatus of claim 1 wherein said universal interface further comprises an optical interface, wherein said docking station receives said optical interface, and wherein said optical interface couples an external source of optical energy to said first face of said chip interface.

5. The apparatus of claim 1 wherein said first face of said chip interface and said outlet face of said fluidic interface are in parallel, opposed relation to one another.

6. The apparatus of claim 1 wherein said chip interface is disposed within a housing, wherein said housing provides EMI shielding.

7. The apparatus of claim 6 further comprising an electrical component, wherein said electrical component is coupled to said micro-fluidic chip, and wherein said electrical component is selected from the group consisting of an amplifier, a controller, a logic element, a memory, and a sensor.

8. The apparatus of claim 6 wherein said housing includes an optical window, wherein said optical window provides a direct optical path between said microfluidic chip and an external optical source.

9. The apparatus of claim 1 wherein said chip interface is disposed within a housing, and wherein said housing includes an optical window, and further wherein said optical window is disposed on a face of said housing that is orthogonal to said first face of said chip interface.

10. The apparatus of claim 9 wherein said face of said housing is substantially parallel to said inlet face of said fluidic interface.

11. The apparatus of claim 1 wherein said docking station comprises a passive-restraint system for locating and securing said chip interface to said docking station.

12. The apparatus of claim 1 further comprising said micro-fluidic chip.

13. The apparatus of claim 12 wherein said micro-fluidic chip is a capillary electrophoresis chip.

14. An apparatus comprising a universal interface, wherein said universal interface comprises:
a chip assembly, wherein said chip assembly receives a micro-fluidic chip and is physically adapted to provide an environment that is substantially fluid-tight for said microfluidic chip, and wherein said chip assembly comprises a chip interface, and wherein said chip interface comprises:
a first face;
a second face, wherein said second face is orthogonal to said first face and wherein said micro-fluidic chip abuts said second face;
a fluidic port, wherein said fluidic port couples fluid that is received at said first face to said micro-fluidic chip at said second face;
an electrical conductor, wherein said electrical conductor couples electrical energy that is received at said first face to said micro-fluidic chip at said second face.

15. The apparatus of claim 14 wherein said fluidic port is self sealing.

16. The apparatus of claim 14 wherein said chip assembly comprises an optical window, wherein said optical window provides a direct optical path between said microfluidic chip and an optical source that is external to said chip assembly.

17. The apparatus of claim 14 wherein said chip assembly further comprises an optical interface, wherein said optical interface couples a optical energy that is received at said first face to said micro-fluidic chip at said second face.

18. The apparatus of claim 14 wherein the universal interface further comprises a docking station, wherein said docking station receives said chip assembly, and wherein said docking station is physically adapted to route said fluid and said electrical energy to said chip assembly.

19. The apparatus of claim 18 wherein said physical adaptation comprises a fluidic interface that couples to said fluidic port on said chip interface, wherein said fluidic interface receives fluid from an external source.

20. The apparatus of claim 18 wherein said physical adaptation comprises a first electrical interface that couples to said electrical conductor, wherein said first electrical interface receives electrical energy from an external source.

* * * * *

UNITED STATES PATENT AND TRADEMARK OFFICE
CERTIFICATE OF CORRECTION

PATENT NO. : 7,582,263 B2  Page 1 of 1
APPLICATION NO. : 11/044542
DATED : September 1, 2009
INVENTOR(S) : Prak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1223 days.

Signed and Sealed this

Fourteenth Day of September, 2010

David J. Kappos
*Director of the United States Patent and Trademark Office*